(12) United States Patent
Garrison et al.

(10) Patent No.: US 8,545,552 B2
(45) Date of Patent: Oct. 1, 2013

(54) SYSTEMS AND METHODS FOR TRANSCATHETER AORTIC VALVE TREATMENT

(75) Inventors: Michi E. Garrison, Half Moon Bay, CA (US); Tony M. Chou, Hillsborough, CA (US); Gregory M. Hyde, Menlo Park, CA (US)

(73) Assignee: Silk Road Medical, Inc., Sunnyvale, CA (US)

(*) Notice: Subject to any disclaimer, the term of this patent is extended or adjusted under 35 U.S.C. 154(b) by 308 days.

(21) Appl. No.: 13/034,513

(22) Filed: Feb. 24, 2011

(65) Prior Publication Data
US 2011/0213459 A1 Sep. 1, 2011

Related U.S. Application Data

(60) Provisional application No. 61/308,606, filed on Feb. 26, 2010.

(51) Int. Cl.
*A61F 2/06* (2013.01)

(52) U.S. Cl.
USPC ......... 623/2.11; 623/2.1; 623/2.14; 623/2.18; 623/2.23; 604/6.14; 604/171; 604/509; 604/96.01

(58) Field of Classification Search
USPC .................... 623/2.11, 2.13, 2.14, 2.18, 2.23, 623/2.24; 604/6.14, 171, 96.01, 509
See application file for complete search history.

(56) References Cited

U.S. PATENT DOCUMENTS

| | | | |
|---|---|---|---|
| 6,071,271 A * | 6/2000 | Baker et al. | 604/500 |
| 6,165,162 A * | 12/2000 | Safar et al. | 604/508 |
| 6,423,032 B2 | 7/2002 | Parodi | |
| 6,454,799 B1 | 9/2002 | Schreck | |
| 6,595,953 B1 | 7/2003 | Coppi et al. | |
| 6,837,881 B1 | 1/2005 | Barbut | |
| 7,083,594 B2 | 8/2006 | Coppi | |
| 8,182,530 B2 * | 5/2012 | Huber | 623/2.11 |
| 8,287,583 B2 * | 10/2012 | LaDuca et al. | 623/1.11 |
| 2001/0044598 A1 | 11/2001 | Parodi | |
| 2003/0135257 A1 | 7/2003 | Taheri | |
| 2005/0148997 A1 * | 7/2005 | Valley et al. | 604/509 |
| 2005/0154349 A1 | 7/2005 | Renz | |
| 2006/0020327 A1 | 1/2006 | Lashinski et al. | |
| 2006/0155366 A1 | 7/2006 | LaDuca et al. | |
| 2008/0065145 A1 | 3/2008 | Carpenter | |
| 2009/0326575 A1 | 12/2009 | Galdonik et al. | |
| 2011/0034986 A1 | 2/2011 | Chou et al. | |
| 2011/0257577 A1 * | 10/2011 | Lane et al. | 604/6.11 |

OTHER PUBLICATIONS

Henry et al. (1999) "Carotid stenting with cerebral protection: First clinical experience using the PercuSurge GuardWire System" *J. Endovasc. Surg.* 6:321-331.

* cited by examiner

*Primary Examiner* — Vy Q Bui
(74) *Attorney, Agent, or Firm* — Fred C. Hernandez; Mintz Levin Cohn Ferris Glovsky and Popeo, P.C.

(57) ABSTRACT

Devices and methods are configured to allow transcervical or subclavian access via the common carotid artery to the native aortic valve, and implantation of a prosthetic aortic valve into the heart. The devices and methods also provide means for embolic protection during such an endovascular aortic valve implantation procedure.

11 Claims, 17 Drawing Sheets

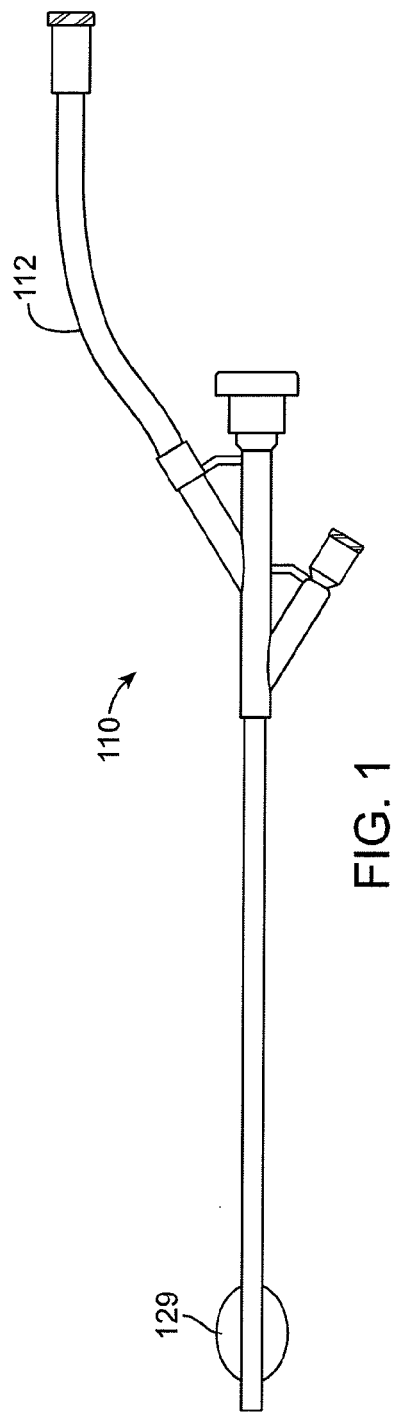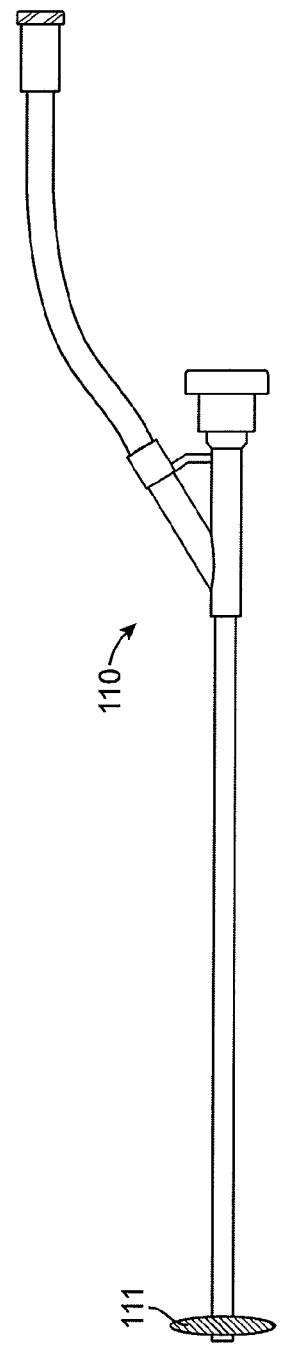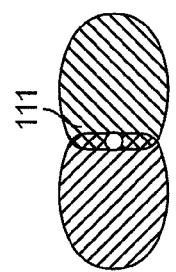

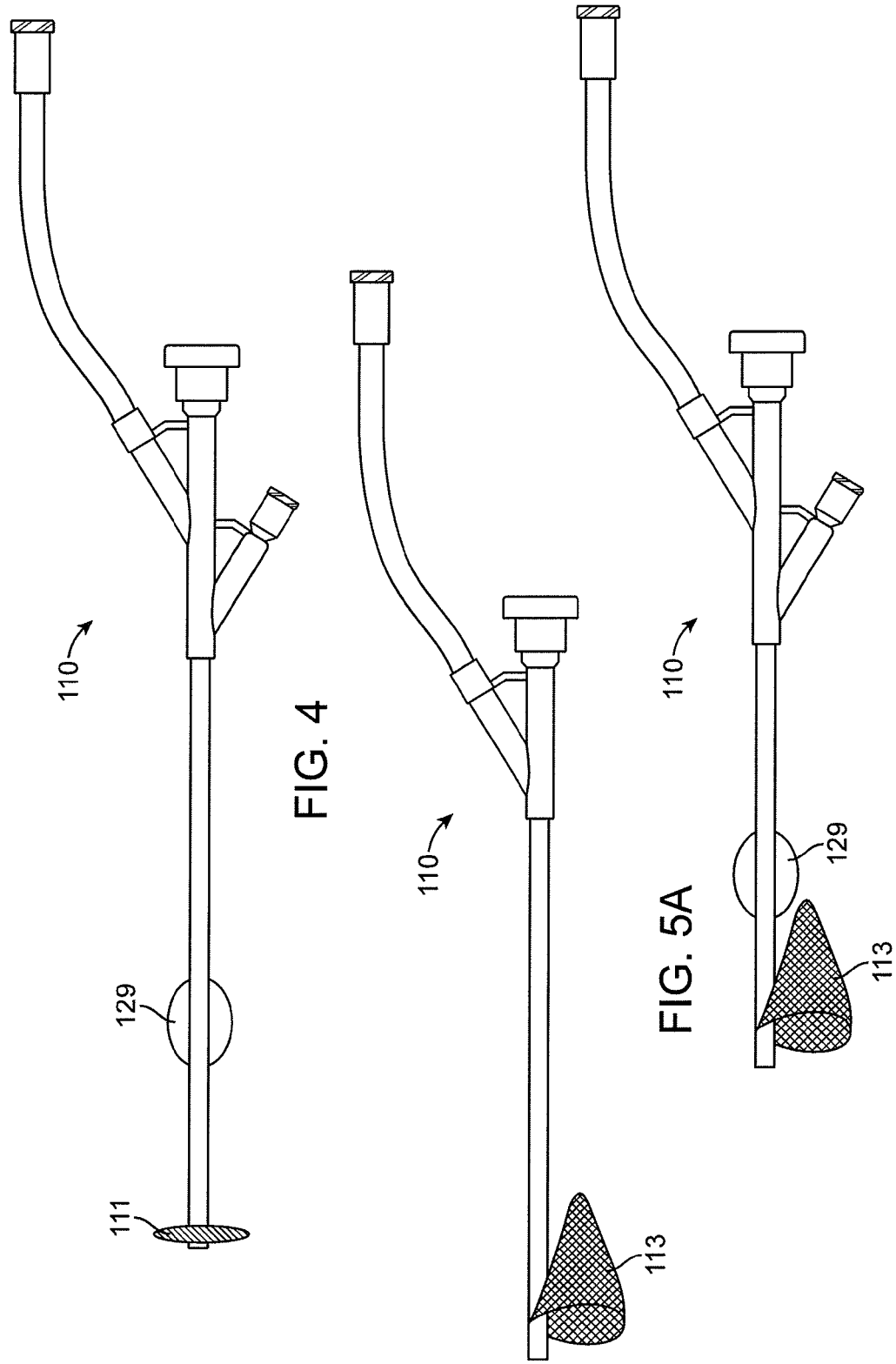

SYSTEMS AND METHODS FOR TRANSCATHETER AORTIC VALVE TREATMENT

REFERENCE TO PRIORITY DOCUMENT

This application claims priority of U.S. Provisional Patent Application Ser. No. 61/308,606, filed on Feb. 26, 2010. The disclosure of the Provisional Patent Application is hereby incorporated by reference in its entirety.

BACKGROUND

The present disclosure relates to methods and devices for replacing heart valves.

Patients with defective aortic heart valves are often candidates for a replacement heart valve procedure. The conventional treatment is the surgical replacement of the heart valve with a prosthetic valve. This surgery involves a gross thorocotomy or median sternotomy, cardiopulmonary bypass and cardiac arrest, surgical access and excision of the diseased heart valve, and replacement of the heart valve with a prosthetic mechanical or tissue valve. Valves implanted in this manner have historically provided good long term outcomes for these patients, with durability of up to ten or fifteen years for tissue valves, and even longer for mechanical valves. However, heart valve replacement surgery is highly invasive, can require lengthy recovery time, and is associated with short and long term complications. For high surgical risk or inoperable patients, this procedure may not be an option.

Recently, a minimally invasive approach to heart valve replacement has been developed. This approach, known as transcatheter aortic valve implantation (TAVI), relies on the development of a collapsible prosthetic valve which is mounted onto a catheter-based delivery system. This type of prosthesis can be inserted into the patient through a relatively small incision or vascular access site, and may be implanted on the beating heart without cardiac arrest. The advantages of this approach include less surgical trauma, faster recovery time, and lower complication rates. For high surgical risk or inoperable patients, this approach offers a good alternative to conventional surgery. Examples of this technology are the Sapien Transcatheter Valve (Edwards Lifesciences, Irvine, Calif.) and the CoreValve System (Medtronic, Minneapolis, Minn.). U.S. Pat. No. 6,454,799, which is incorporated herein by reference in its entirety, describes examples of this technology.

There are two main pathways for valves inserted using the TAVI approach. The first is a vascular approach via the femoral artery (referred to as a transfemoral approach), either percutaneously or through a surgical cut-down and arteriotomy of the femoral artery. Once placed into the femoral artery, the valve mounted on the delivery system is advanced in a retrograde manner up the descending aorta, around the aortic arch, and across the ascending aorta in order to be positioned across the native aortic valve. Transfemoral aortic valve delivery systems are typically over 90 cm in length and require the ability to navigate around the aortic arch. The relatively small diameter of the femoral artery and the frequent presence of atherosclerotic disease in the iliofemoral anatomy limits the maximum diameter of the delivery system to about 24 French (0.312") in diameter. The second pathway, termed transapical, involves accessing the left ventricle through the apex of the heart via a mini-thorocotomy, and advancing the valve delivery system in an antegrade fashion (in the same direction as blood flow) to the aortic valve position. This pathway is much shorter and straighter than the transfemoral path, but involves a surgical puncture and subsequent closure of the wall of the heart.

Other approaches have been described, including access from the subclavian artery, and direct puncture of the ascending aorta via a mini-thorocotomy. The subclavian approach (transsubclavian approach) has been used when the transfemoral route is contra-indicated, but may block flow to the cerebral vessel through the ipsilateral common carotid artery. A direct aortic puncture is usually considered if all other routes must be excluded due to anatomic difficulties including vascular disease. Puncture of the aortic wall, and subsequent closure, carries associated surgical risk including aortic dissection and rupture.

The transfemoral approach to the aortic valve, as opposed to the transapical approach, is a generally more familiar one to the medical community. Accessing the ascending aorta from the femoral artery is standard procedure for interventional cardiologists. Balloon valvuloplasty procedures via the transfemoral approach have been performed for years. The surgical approaches such as the transapical access or direct aortic puncture are less familiar and require practitioners with both surgical and endovascular skills; techniques for the surgical approaches are still evolving and whether they offer advantages over the transfemoral and transsubclavian methods have yet to be determined. However, problems also exist with the transfemoral and transsubclavian approaches. One is that the desired access vessel is often too small and/or is burdened with atherosclerotic disease, which precludes the artery as an access point. A second problem is that the pathway from the access point to the aortic valve usually involves one or more major turns of at least 90° with a relatively tight radii of curvature, 0.5" or less, requiring a certain degree of flexibility in the delivery system. This flexibility requirement restricts the design parameters of both the valve and the delivery system, and together with the required length of the delivery system reduces the level of control in accurately positioning the valve.

Both the transfemoral and transapical approaches have as potential complications the dislodgement of atherosclerotic and/or thrombotic debris, so-called "embolization" or the creation of "embolic debris," during both access maneuvers and implantation of the prosthetic valve. The most serious consequence of embolic debris is that it travels with the blood flow to the brain via one or more of the four primary conduits to the cerebral circulation, namely the right and left carotid arteries and the right and left vertebral arteries. Transfemoral TAVI procedures require passage of large device and delivery system components through the aortic arch and across the origins of the head and neck vessels that supply blood flow to the carotid and vertebral arteries, potentially loosening, fragmenting, and dislodging debris during its route to the aortic valve. The transapical TAVI procedure involves a puncture of the heart wall, which may generate embolic debris from the wall of the ventricle or ascending aorta, or may form thrombus or clot at the apical puncture location. During the vigourous motion of the beating heart, this clot can break free and travel to the brain as well. Both approaches require significant manipulation while the prosthetic valve is being placed: the TAVI implant and delivery system moves back and forth across the native aortic valve, potentially dislodging more debris from the diseased valve itself. With expansion of the valve implant, the native aortic valve is compressed and moved out of the stream of the cardiac output, another moment when the shearing and tearing of the native valve can free more debris to embolize to the brain.

Recently, there has been described an embolic filter protection device for use with TAVI procedures, as referenced in U.S. Patent Application Publication No. 20080065145, which is incorporated herein by reference in its entirety. This device places a temporary screen over the ostium of the head and neck vessels to prevent passage of embolic particles while allowing blood flow into the vessels. While this device may offer some protection from larger embolic particles, it requires an additional vascular access and device deployment, adding to the cost and time of the procedure, and does not facilitate the passage of the prosthetic valve itself. Moreover, it does not provide protection during filter placement and retrieval; since the filter is deployed against the wall of the aorta, there is a high chance that the filter manipulation itself will be the cause of embolic complications.

SUMMARY OF INVENTION

There is a need for an access system for endovascular prosthetic aortic valve implantation that provides a generally shorter and straighter access path than current systems and methods. This would allow the use of shorter and more rigid delivery systems which would offer a greater degree of control and easier placement of the aortic valve. There is also a need for an access system that provides protection from cerebral embolic complications during the procedure.

Disclosed herein are devices and methods that allow transcervical or subclavian access via the common carotid artery to the native aortic valve, and implantation of a prosthetic aortic valve into the heart. The devices and methods also provide means for embolic protection during such an endovascular aortic valve implantation procedure.

In one aspect, there is disclosed a system for aortic valve treatment, comprising: an arterial access sheath adapted to be introduced into an access site at the left common carotid artery, right common carotid artery, left subclavian artery, or right subclavian artery, wherein the arterial access sheath includes an internal lumen sized and shaped to receive a valve delivery system configured to deliver a prosthetic valve into the heart through the arterial access sheath; and an occlusion element on the arterial access sheath, the occlusion element adapted to occlude an artery.

In another aspect, there is disclosed a system for aortic valve treatment, comprising: an arterial access sheath adapted to be introduced into an access site at the left common carotid artery, right common carotid artery, left subclavian artery, or right subclavian artery, wherein the arterial access sheath has an internal lumen sized and shaped to receive a valve delivery system configured to deliver a prosthetic valve into the heart through the arterial access sheath; and a filter coupled to the arterial access sheath to provide embolic protection.

In another aspect, there is disclosed a system for transcervical aortic valve treatment, comprising: an arterial access sheath adapted to be introduced into an access site at the left common carotid artery, right common carotid artery, left subclavian artery, or right subclavian artery, wherein the arterial access sheath has an internal lumen sized and shaped to receive a valve delivery system adapted to deliver a prosthetic valve into the heart through the arterial access sheath; and a return shunt fluidly connected to the arterial access sheath, wherein the shunt provides a pathway for blood to flow from the arterial access sheath to a return site.

In another aspect, there is disclosed a system for aortic valve treatment, comprising: an arterial access sheath adapted to be introduced into an access site at the left or right common carotid artery, or left or right subclavian artery, wherein the arterial access sheath has a first lumen sized and shaped to receive a valve delivery system configured to deliver a prosthetic valve into the heart through the arterial access sheath; a Y-arm disposed at a proximal region of the arterial access sheath; and a flow shunt fluidly connected to the Y-arm, wherein the flow shunt is adapted to perfuse the distal carotid artery.

In another aspect, there is disclosed a system for aortic valve treatment, comprising: an arterial access sheath adapted to be introduced into an access site at the left or right common carotid artery, or left or right subclavian artery, wherein the arterial access sheath has an internal lumen sized and shaped to receive a valve delivery system configured to deliver a prosthetic valve into the heart through the arterial access sheath; a side opening in the arterial access sheath adapted to allow blood flow antegrade into the tip of the access sheath and out the side opening to perfuse the distal carotid artery; and a dilator which is inside the access sheath during insertion of the access sheath into the artery and which prevents flow through the sheath and out the side opening during access sheath insertion.

In another aspect, there is disclosed a method of treating an aortic valve, comprising: forming a penetration at the neck of a patient in a wall of a common carotid artery; introducing an access sheath through the penetration; occluding the artery; inserting a guide wire through the access sheath and across the native aortic valve; and introducing a prosthetic valve through the access sheath and percutaneously deploying the prosthetic valve at or near the position of the native aortic valve.

In another aspect, there is disclosed a method of treating an aortic valve, comprising: forming a penetration at the neck of a patient in a wall of a common carotid artery; introducing an access sheath through the penetration; deploying a filter to provide embolic protection in an artery; inserting a guide wire through the access sheath and across the native aortic valve; and introducing a prosthetic valve through the access sheath and deploying the prosthetic valve at or near the position of the native aortic valve.

Other features and advantages should be apparent from the following description of various embodiments, which illustrate, by way of example, the principles of the invention.

BRIEF DESCRIPTION OF THE DRAWINGS

FIG. 1 shows a side view of an exemplary access sheath having an occlusion element mounted on the sheath.

FIG. 2 shows a side view of an exemplary access sheath having a filter element mounted on the sheath.

FIG. 3 shows a front view of the filter element.

FIGS. 4, 5A, and 5B show alternate embodiments of the access sheath.

DETAILED DESCRIPTION

Figure 6:
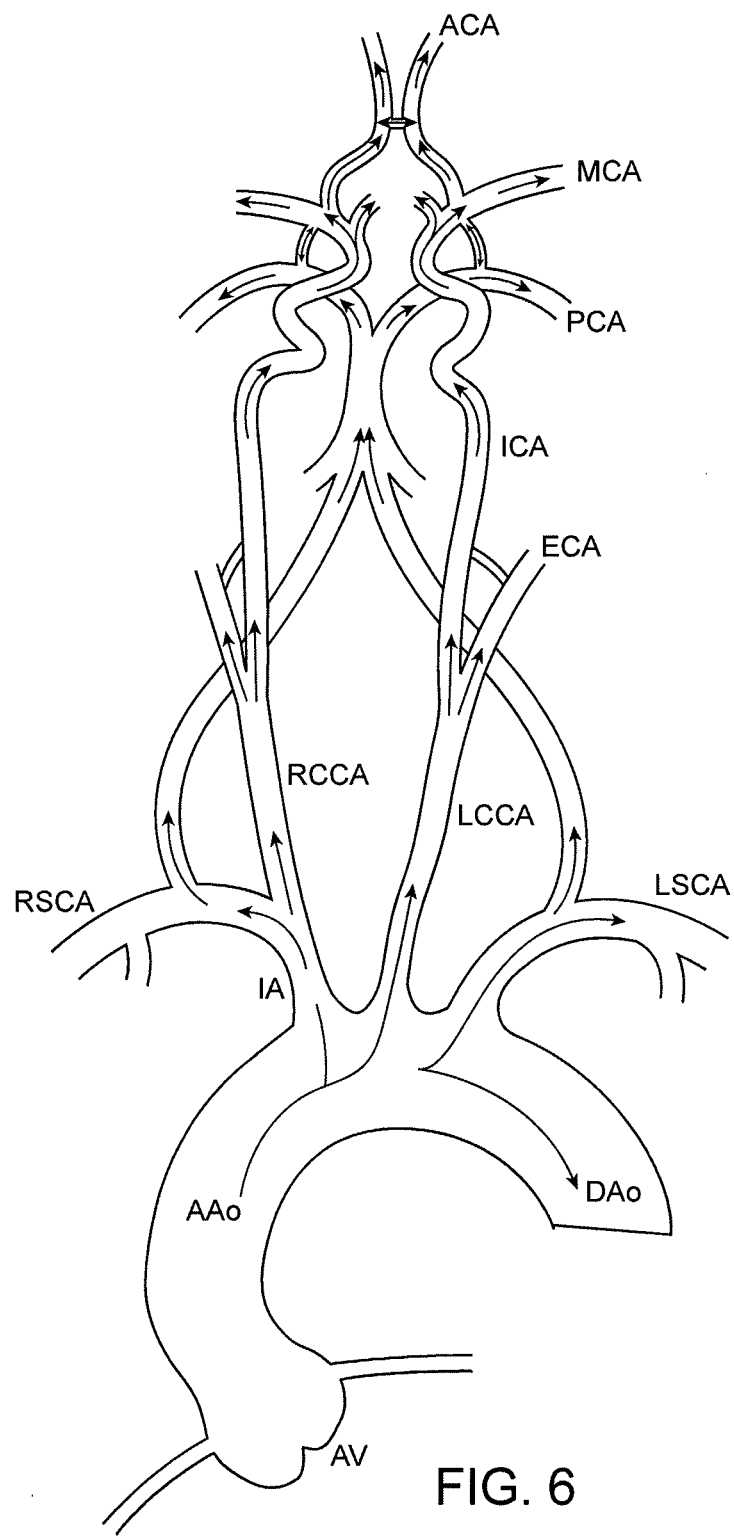
FIG. 6 schematically depicts a view of the vasculature showing normal circulation.

Disclosed herein are devices and methods that allow arterial access, such as transcervical access via the common carotid artery, or subclavian access via the subclavian artery to the native aortic valve, and implantation of a prosthetic aortic valve into the heart. The devices and methods also provide means for embolic protection during such an endovascular aortic valve implantation procedure.

In an embodiment, transcervical or subclavian access to the aortic valve is accomplished via either a percutaneous puncture or direct cut-down to the artery. A cut-down may be advantageous due to the difficulty of percutaneous vessel closure of larger arteriotomies in the common carotid artery. If desired, a pre-stitch may be placed at the arteriotomy site to facilitate closure at the conclusion of the procedure. An access sheath with associated dilator and guidewire is provided which is sized to fit into the common carotid or subclavian artery. The access sheath is inserted into the artery inferiorly towards the aortic arch. Either the left or the right common carotid or subclavian artery may be selected as the access site, based on factors including, for example, the disease state of the proximal artery and/or the aorta and the angle of entry of the carotid or innominate artery into the aorta. The carotid artery may then be occluded distal to the access site. If the access is via a direct surgical cut-down and arteriotomy, the occlusion may be accomplished via a vascular clamp, vessel loop, or Rummel tourniquet. Alternately, the access sheath itself may include an occlusion element adapted to occlude the artery, for example an occlusion balloon, to prevent embolic particulates from entering the carotid artery distal to the access site during the procedure.

FIG. 1 shows a side view of an exemplary arterial access sheath 110 formed of an elongate body having an internal lumen. In an embodiment, the sheath has a working length of 10-60 cm. The lumen of the sheath has an inner diameter large enough to accommodate insertion of an endovascular valve delivery system, such as a 18 French to 22 French (0.236" to 0.288") system. In an embodiment, the delivery system has an inner diameter as low as about 0.182" The access sheath 110 can have an expandable occlusion element 129 positioned on the access sheath. The occlusion element 129 is configured to be expanded to a size for occluding flow through the artery. The occlusion element 129 may be placed anywhere in the artery. In an embodiment, the occlusion element is an occlusion balloon.

Once the sheath 110 is positioned in the artery, the occlusion element 129 is expanded within the artery to occlude the artery and possibly anchor the sheath into position. The arterial access sheath 110 may include a Y-arm for delivery of contrast or saline flush, for aspiration, and/or may be fluidly connected to a shunt, wherein the shunt provides a pathway for blood to flow from the arterial access sheath 110 to a return site such as a venous return site or a collection reservoir. In this regard, a retrograde or reverse blood flow state may be established in at least a portion of the artery. The sheath 110 may also include a Y-arm for inflation of the occlusion balloon via an inflation lumen, and a hemostasis valve for introduction of an endovascular valve delivery system into the sheath. The endovascular valve delivery system may include a prosthetic valve and a delivery catheter. In an embodiment, the delivery catheter has a working length of 30, 40, 60, 70, or 80 cm.

In an embodiment, aspiration may be applied to the artery via the access sheath 110. In this regard, the access sheath 110 can be connected via a Y-arm 112 to an aspiration source, so that embolic debris may be captured which may otherwise enter the remaining head and neck vessels, or travel downstream to lodge into peripheral vessels. The aspiration source may be active, for example a cardiotomy suction source, a pump, or a syringe. Alternately, a passive flow condition may be established, for example, by fluidly connecting the Y-arm 112 to a shunt, which in turn is connected to a lower-pressure source such as a collection reservoir at atmospheric or negative pressure, or a venous return site in the patient. The passive flow rate may be regulated, for example, by controlling the restriction of the flow path in the shunt.

In an embodiment, the access system may be equipped with one or more embolic protection elements to provide embolic protection for one or both carotid arteries. For example, a filter may be included in the access system to provide embolic protection for one or both carotid arteries. In a variation of this embodiment, the filter is deployed via the contralateral carotid, brachial or subclavian artery, and positioned in the aortic arch across the ostium. If the sheath access site is the left common carotid artery, the filter may be positioned across the ostium of the innominate (also known as brachiocephalic) artery. If the sheath access site is the right common carotid artery, the filter may be positioned across the ostium of the left common carotid artery. In a variation of this embodiment, the filter is deployed across both the innominate and left common carotid artery, or across all three head and neck vessels (innominate artery, left common carotid artery, and left subclavian artery). The filter element may be built-in to the access sheath 110. Or, the filter element may be a separate element which is compatible with the access sheath 110. For example, the filter element may be a coaxial element which is slideably connected to the access sheath or an element which is placed side-by-side with the access sheath. The filter element may comprise an expandable frame, so that it may be inserted into the artery in a collapsed state, but then expanded at the target site to position the filter element across the opening of the artery or arteries. FIG. 2 shows a side view of an exemplary access sheath 110 having a filter element 111 mounted on the sheath. FIG. 3 shows a front view of the filter element 111 showing an exemplary profile of the filter element 111. In the embodiment of FIG. 3, the filter element 111 is sized and shaped to fit within and block the head and neck vessels. In an embodiment, the deployed filter has a long dimension of about 2, 3, 4, or 5 cm and a short dimension of about 1, 1.5, or 2 cm. The profile shown in FIG. 3 is for example and it should be appreciated that the shape of the filter element 111 may vary. For example, the shape of the filter element may be oval, round, elliptical, or rectangular. The filter material may be woven or knitted textile material, or may be a perforated polymer membrane such as polyurethethane. The filter porosity may be 40, 100, 150, 200, or 300 microns, or any porosity in between. The expandable frame of the filter element may be made from spring material such as stainless steel or nitinol wire or ribbon.

In the embodiment with the filter element, occlusion and/or aspiration means may still be part of the system, to provide embolic protection during filter deployment before the valve implantation and filter retrieval after valve implantation. The filter element itself may be a primary method of embolic protection during the implantation procedure. The sheath 110 may also be equipped with both an occlusion element 129 and a filter element 111, as shown in FIG. 4.

In another variation of this embodiment, shown in FIG. 5A, the sheath 110 includes an aortic filter element 113 which is sized and shaped to be deployed across the ascending aorta and thus protect all the head and neck vessels from embolic debris. The shape of the filter element may vary. In an embodiment, the shape of the filter element may be a cone or a closed-end tube. The expandable frame of the filter frame is sized and shaped to traverse the entire diameter of the aorta when deployed. For example the expandable frame may be a loop which can expand from 12 to 30 mm in diameter. Alternately, the expandable frame may be a series of struts connected at one or both ends and which expand outwardly to deploy the filter element across the diameter of the aorta. The filter material may be woven or knitted textile material, or may be a perforated polymer membrane such as polyurethethane. The filter porosity may be about 40, 100, 150, 200, or 300 microns, or any porosity in between. The expandable frame of the filter element may be made from spring material such as stainless steel or nitinol wire or ribbon. As with the previous variation, occlusion and aspiration means may be included in this variation to provide protection during filter deployment and filter retrieval. The aortic filter element 113 may be integral to the sheath, or be a separate device which is compatible with the sheath, for example may be coaxial or side-by-side with the access sheath. As shown in FIG. 5B, an embodiment of the sheath 110 may include both an aortic filter element 113 and an occlusion element 129.

FIG. 6 schematically depicts a view of the vasculature showing normal antegrade circulation. The blood vessels are labeled as follows in FIG. 6: ACA: anterior cerebral artery; MCA: middle cerebral artery; PCA: posterior cerebral artery; ICA: internal carotid artery; ECA: external carotid artery; LCCA: left common carotid artery; RCCA: right common carotid artery; LSCA: left subclavian artery; RSCA: right subclavian artery; IA: innominate artery; AAo: Ascending aorta; DAo: descending aorta; AV: aortic valve.

Figure 7:
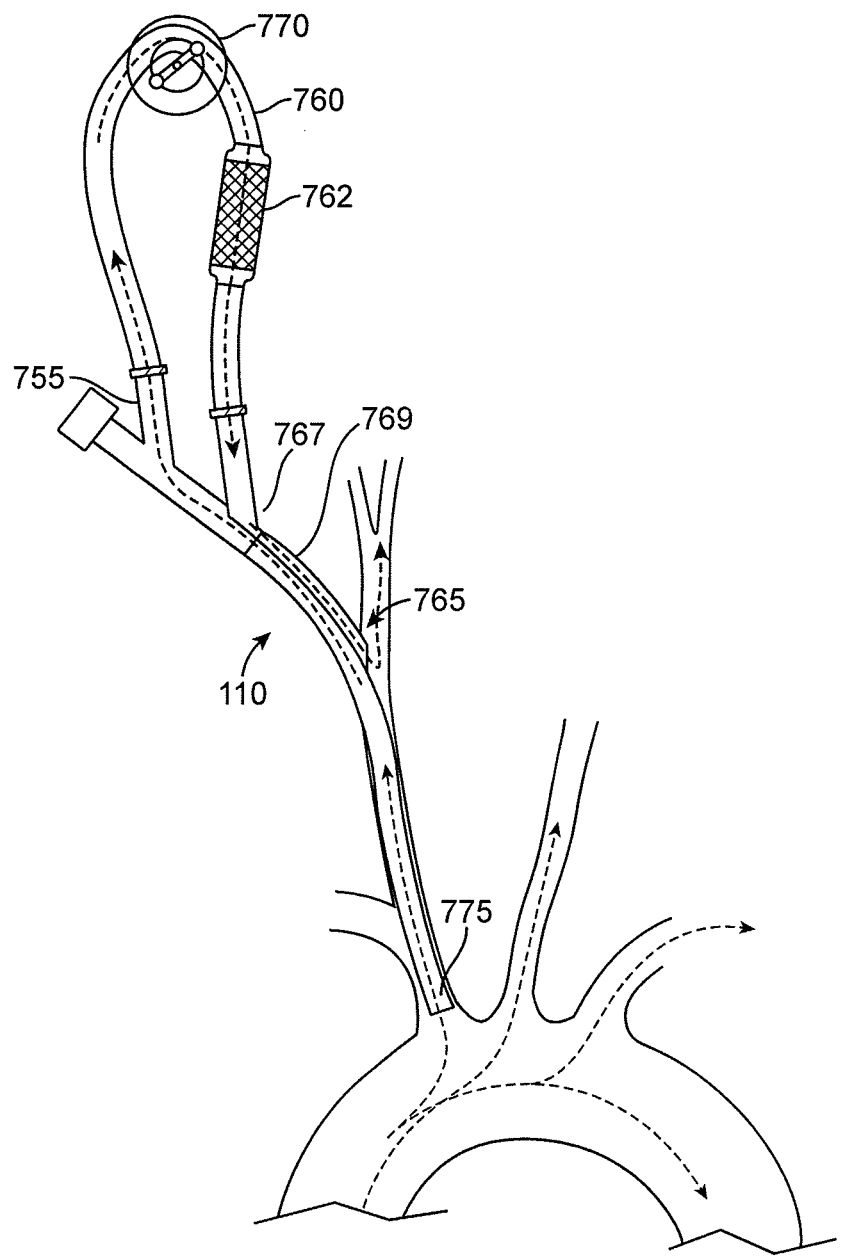
FIG. 7 shows another embodiment of an access sheath deployed in the vasculature.

In certain situations, it may be desirable to provide a mechanism for perfusing the carotid artery upstream of the entry point of the access sheath 110 into the carotid or innominate artery. If the access sheath 110 is similar in size to the carotid or innominate artery, flow through the artery may be essentially blocked when the sheath is inserted into the artery. In this situation, the upstream cerebral vessels may not be adequately perfused due to blockage of the carotid artery by the sheath. In an embodiment of the access sheath 110, the sheath includes a mechanism to perfuse the upstream carotid and cerebral vessels. FIG. 7 shows an exemplary embodiment of such an access sheath 110 deployed in the vasculature. A Y-arm 755 on the proximal region of the access sheath 110 is connected to a flow shunt 760 that is configured to reintroduce blood flow into the carotid artery at a location 765 upstream from the access point into the carotid artery. In this regard, a second Y-arm 767 is fluidly connected to the shunt 760 and to a parallel lumen 769 that re-introduces blood from the shunt 760 into the artery at location 765. When the sheath is positioned, arterial pressure drives blood flow into the distal end 775 of the arterial access sheath and then into the shunt 760 via the Y-arm 755. The blood then flows into the parallel lumen 769 from the shunt and into the carotid artery at the location 765, which is located upstream of the access location into the carotid artery. A filter element 762 may be included in the flow shunt 760 so that emboli generated during the procedure are not perfused into the cerebral artery. The access sheath 110 shown in FIG. 7 may be equipped with an occlusion element if desired. In the event the sheath 110, shunt 760, and lumen 769 create a flow restriction that limits adequate perfusion, the flow shunt 760 may incorporate an active pump 770 to drive perfusion and provide the required level of cerebral perfusion.

Figure 8:
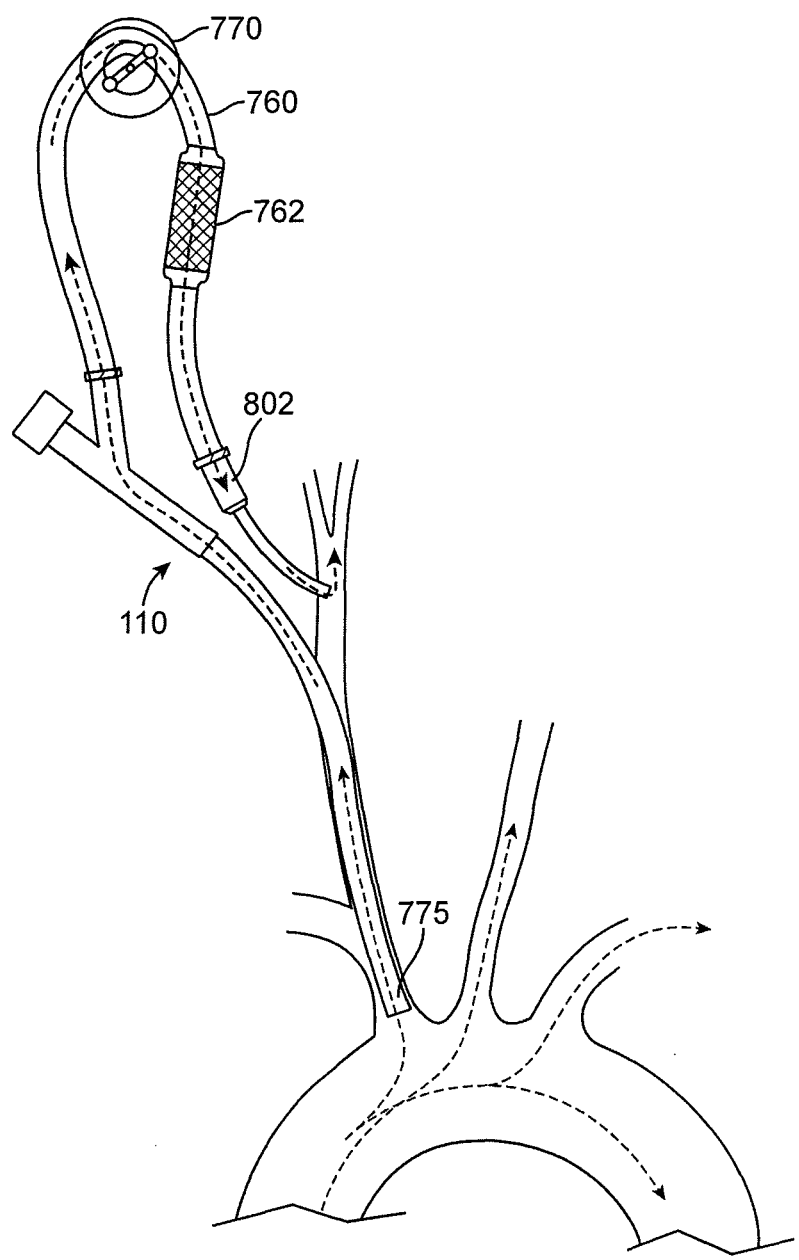
FIG. 8 shows another embodiment of an access sheath deployed in the vasculature.

In another variation, shown in FIG. 8, the flow shunt 760 is connected at its distal end to a second catheter 802 which is sized and shaped to be introduced into the carotid artery distal to arterial access point where the access sheath 110 is introduced. The arterial pressure drives flow into the distal end 775 of the sheath 110, through the shunt 760, through the second catheter 802, and back into the carotid artery upstream from the arterial access point. As above, a filter element 762 may be included in the flow shunt 760 so that emboli generated during the procedure are not perfused into the cerebral artery. The filter element may In the event the sheath 110 and shunt 760 experience flow restriction that limits adequate perfusion, the flow shunt may incorporate an active pump 770 to drive perfusion and provide the required level of cerebral perfusion. Although the figures show sheath insertion in the common carotid artery, a similar sheath may be designed for subclavian access.

Figure 9:
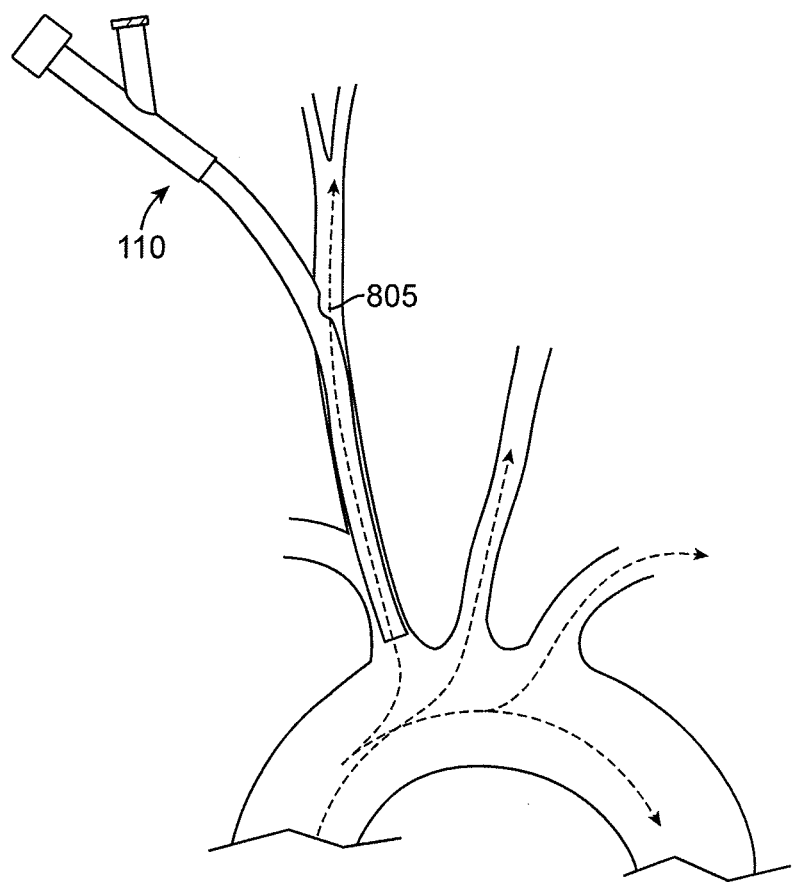
FIG. 9 shows another embodiment of an access sheath deployed in the vasculature.
Figure 10:
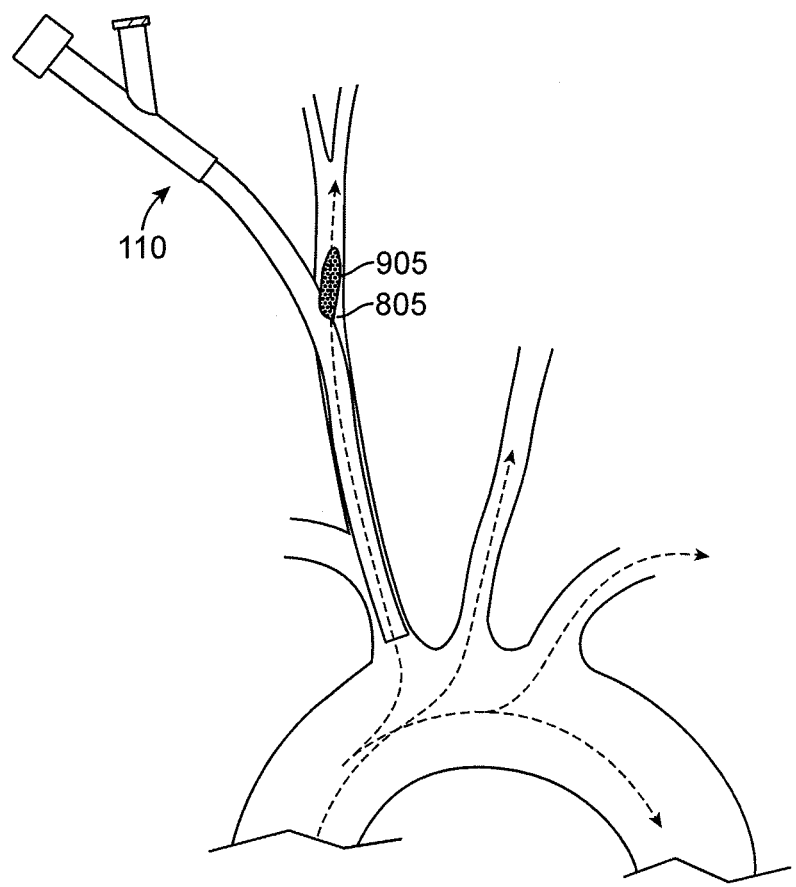
FIG. 10 shows another embodiment of an access sheath deployed in the vasculature.

In another embodiment, the access sheath 110 may have at least one side opening 805 located between the distal end and the proximal end of the sheath 110, as shown in FIG. 9. A dilator may be positioned inside the sheath 110 to block the side opening 805 during insertion of the sheath. The dilator is used to aid in sheath insertion into the artery. When the access sheath 110 is inserted into the artery and the dilator is removed, the dilator no longer blocks the opening 805 so that blood may flow out of the access sheath 110 through the side opening 805 into the distal carotid artery. During introduction of the endovascular valve delivery system through the access sheath 110 and into the artery, the delivery system may restrict the flow through the sheath and artery and may reduce the level of cerebral perfusion. However, this period of the procedure is transient, and reduction of cerebral perfusion during this limited period of time should not present a clinical issue. In a variation of this embodiment as shown in FIG. 10, the side opening 805 may have a filter 905 that covers the opening 805. The filter 905 is configured to capture embolic debris so that the debris does not pass downstream towards the cerebral arteries. The filter 905 may be sized and shaped to bulge out of the sheath 110, so that when the endovascular valve is inserted into the sheath 110, the debris is not pushed forward and out the distal end of the sheath into the artery. In an embodiment, the filter is very thin, perforated film or woven material, similar in composition to embolic distal filter materials. Filter porosity may be about 150, 200, or 250 microns. Though FIGS. 9 and 10 show sheath insertion in the common carotid artery, a similar sheath may be designed for sub-clavian access, in which the sheath insertion site is farther from the carotid artery and the side opening may be placed correspondingly further towards the tip of the sheath.

The sheath in embodiments shown in FIGS. 7-10 may optionally include a positioning element which can be deployed once the sheath is inserted into the blood vessel. The positioning element can be used to position the sheath in the vessel such that the side opening 805 remains in a desired location inside the vessel. This positioning feature may take the form of a deployable protruding member such as a loop, braid, arm, or other protruding feature. This feature may be retracted during sheath insertion into the artery but deployed after the sheath is inserted and the opening is inside the vessel wall. Sheath retention may also be achieved, for example, by an eyelet or other feature in the Y-arm of the access sheath 110 which allows the sheath to be secured to the patient once positioned correctly.

Exemplary methods of use are now described. In an embodiment, a general method includes the steps of forming a penetration from the neck of a patient into a wall of a common carotid artery; introducing an access sheath through the penetration with the tip directed inferiorly towards the ostium of the artery; inserting a guide wire through the access sheath into the ascending aorta and across the native aortic valve; and introducing a prosthetic valve through the access sheath and percutaneously deploying the prosthetic valve at or near the position of the native aortic valve. In an embodiment, the artery is occluded distal (upstream) from the tip of the sheath.

Figure 11:
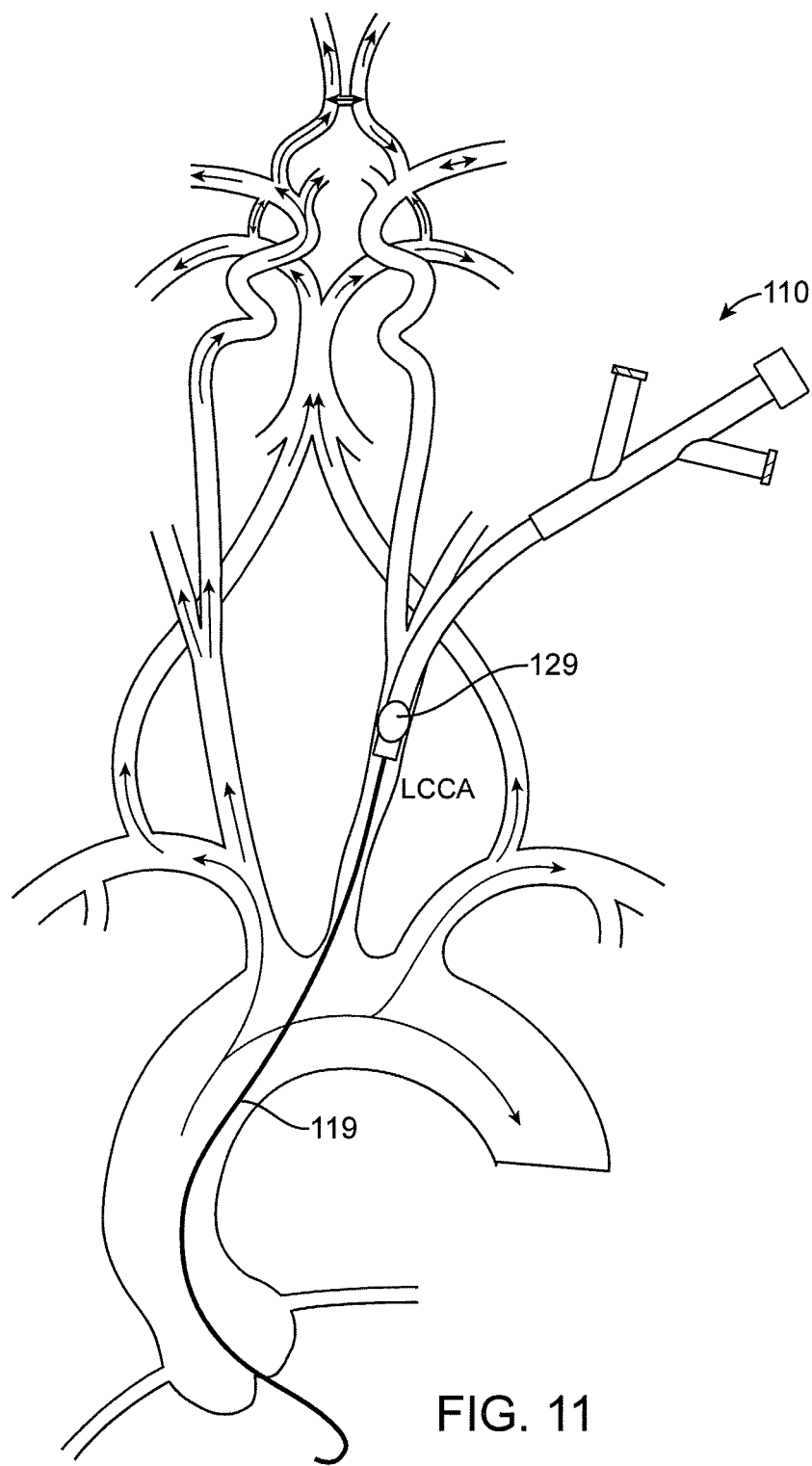
FIG. 11 shows another embodiment of an access sheath deployed in the vasculature with an occlusion element occluding the left common carotid artery.
Figure 12:
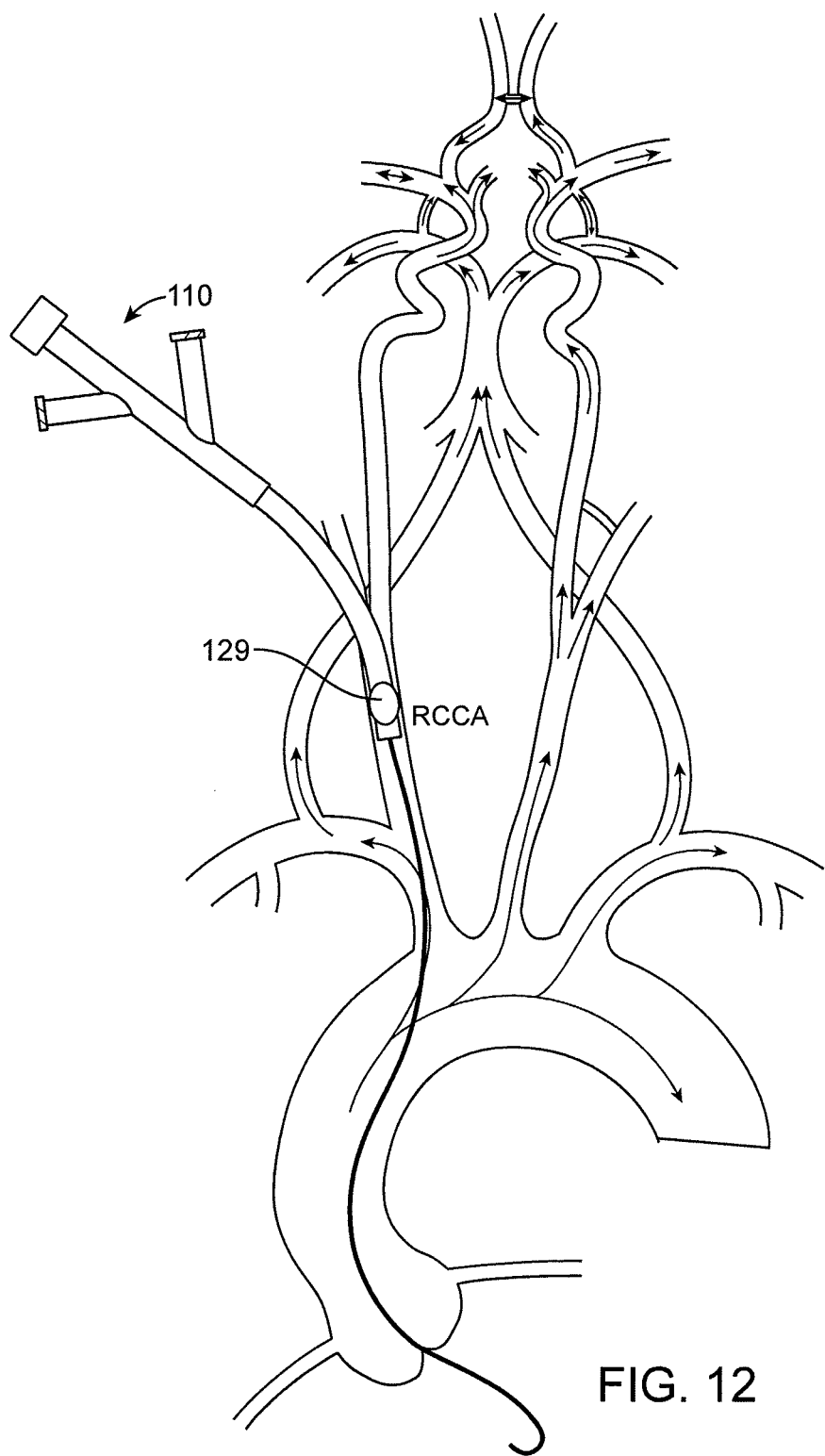
FIG. 12 shows another embodiment of an access sheath deployed in the vasculature with an occlusion element occluding the right common carotid artery.
Figure 13:
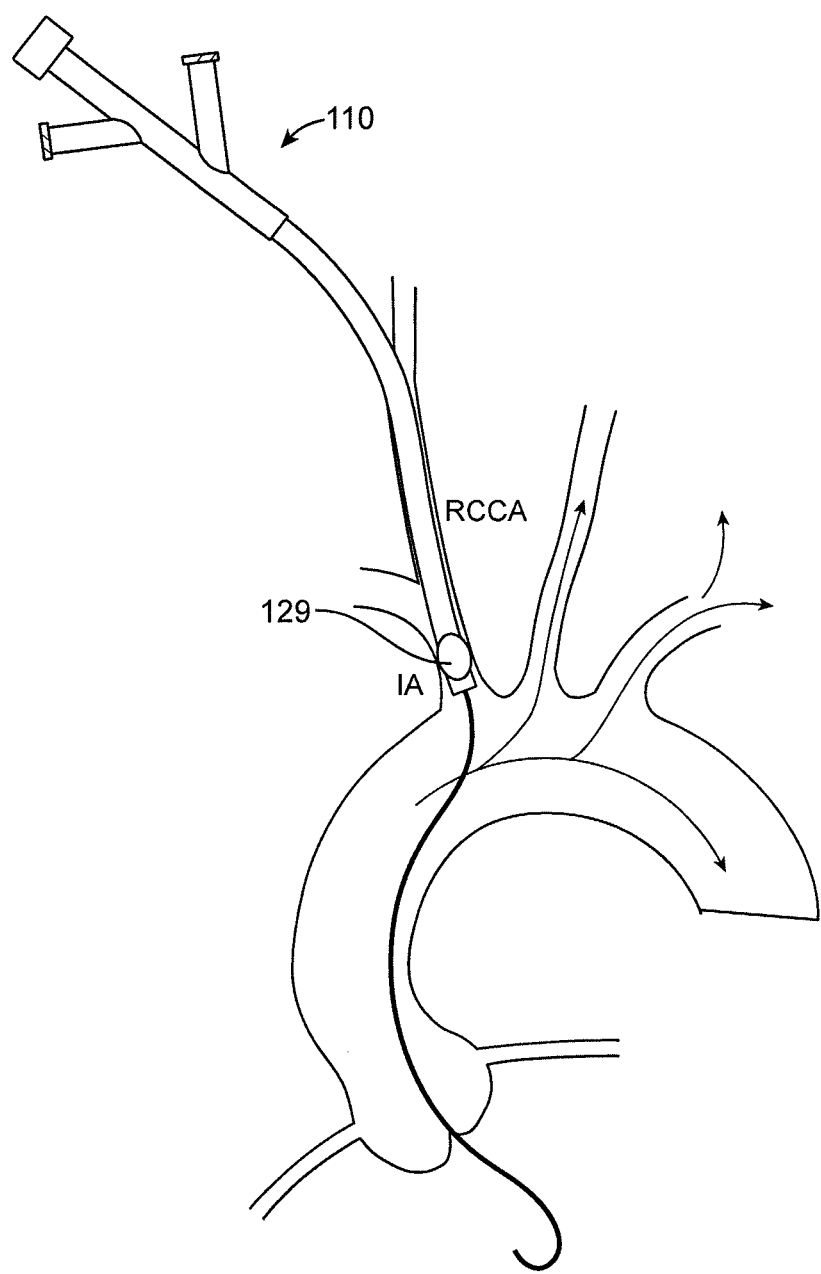
FIG. 13 shows another embodiment of an access sheath deployed in the vasculature with an occlusion element occluding the innominate artery.

In particular, the access sheath 110 is first inserted into the vasculature such as via either a percutaneous puncture or direct surgical cut-down and puncture of the carotid artery. As mentioned, a transcervical approach to the aortic valve may be achieved via the LCCA. Once properly positioned, the occlusion element 129 may be expanded to occlude the LCCA, as shown in FIG. 11. In another embodiment, a transcervical approach to the aortic valve may be achieved via the RCCA, with the occlusion element 129 occluding the RCCA, as shown in FIG. 12. In another embodiment, a transcervical approach to the aortic valve may be achieved via the RCCA, with the occlusion element 129 occluding the innominate artery IA, as shown in FIG. 13. The occlusion achieved via the occlusion element 129 can also be achieved via direct clamping of the carotid vessel, e.g. with a vascular clamp, vessel loop or Rummel tourniquet.

Once the access sheath is positioned and the embolic protection means are deployed via occlusion, aspiration, and/or filter elements, access to the aortic valve is obtained via a guidewire 119 (such as a 0.035" or 0.038" guidewire) inserted into the sheath 110 and directed inferiorly into the ascending aorta and across the native aortic valve. Pre-dilation of the native aortic valve can be performed with an appropriately sized dilation balloon, for example a valvuloplasty balloon, before valve implantation. The guidewire 119 is used to position a balloon across the valve and the balloon is inflated, deflated, and then removed while the guidewire remains in place.

Figure 14:
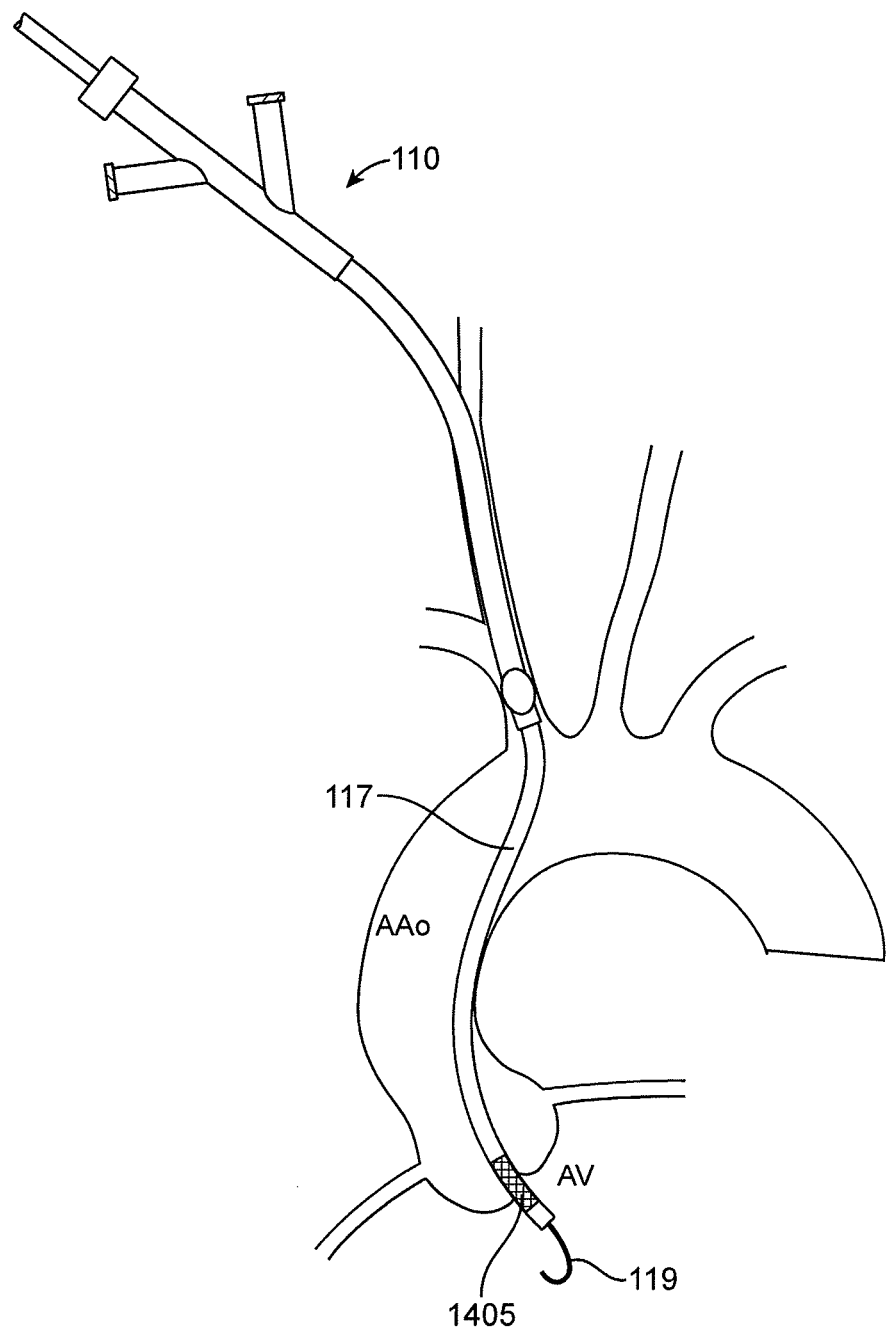
FIG. 14 shows a delivery system deploying an endovascular prosthetic valve via an access sheath 110 and guidewire 119.

An endovascular prosthetic valve 1405 coupled to a delivery system 117 is then inserted through the access sheath 110 over the guidewire 119 and positioned at the site of the native aortic valve (as shown in FIG. 14). The prosthetic valve 1405 is then implanted. In an embodiment, the valve delivery system 117 is as short as 40 cm, and semi rigid as may be required to take 45 degree or less turns over fairly large radii (greater than 0.5") of curvature. Materials for the delivery system may include reinforced, higher durometer, and/or thicker walled materials as compared to current delivery systems to provide this increased rigidity. This increased rigidity, along with the shorter length, allows greater push and torque control in positioning and deploying the prosthetic valve.

At the conclusion of the implantation step, the implanted prosthetic valve 1405 function can be accessed via ultrasound, contrast injection under fluoroscopy, or other imaging means. Depending on the design of the delivery system 117, the prosthetic valve 1405 may be adjusted as needed to achieve optimal valve function and position before final deployment. The delivery system 117 and guidewire 119 are then removed from the access sheath 110. After removal of the delivery system 117 and guidewire 119, the embolic protection elements are removed. Aspiration may continue during this time to capture any embolic debris caught in the sheath tip, occlusion element and/or filter elements.

The access sheath 110 is then removed and the access site is closed. If the access was a surgical cutdown direct puncture, the vessel is closed either via tying off the pre-placed stitch or with manual suturing or with a surgical vascular closure device, as described in more detail below. If the access was percutaneous, percutaneous closure methods and devices may be employed to achieve hemostasis at the access site. In an embodiment, the closure device is applied at the site of the penetration before introducing the arterial access sheath through the penetration. The type of closure device can vary.

The access site described above is either the left or right common carotid artery. Other access sites are also possible, for example the left or right subclavian artery or left or right brachial artery. These arteries may require longer and/or more tortuous pathways to the aortic valve but may offer other advantages over a carotid artery access, for example the ability to work away from the patient's head, the ability to avoid hostile neck anatomy such as previous carotid endarterectomy or other cervical surgery or radiation, or less risky in case of access site complication. In addition, carotid artery disease, or small carotid arteries may preclude common carotid artery access. In the case of any of these access sites, occlusion, aspiration, and/or filtering the head and neck vessels during TAVI may increase the speed and accuracy of the procedure, and decrease the rate of embolic complications.

Figure 15B:
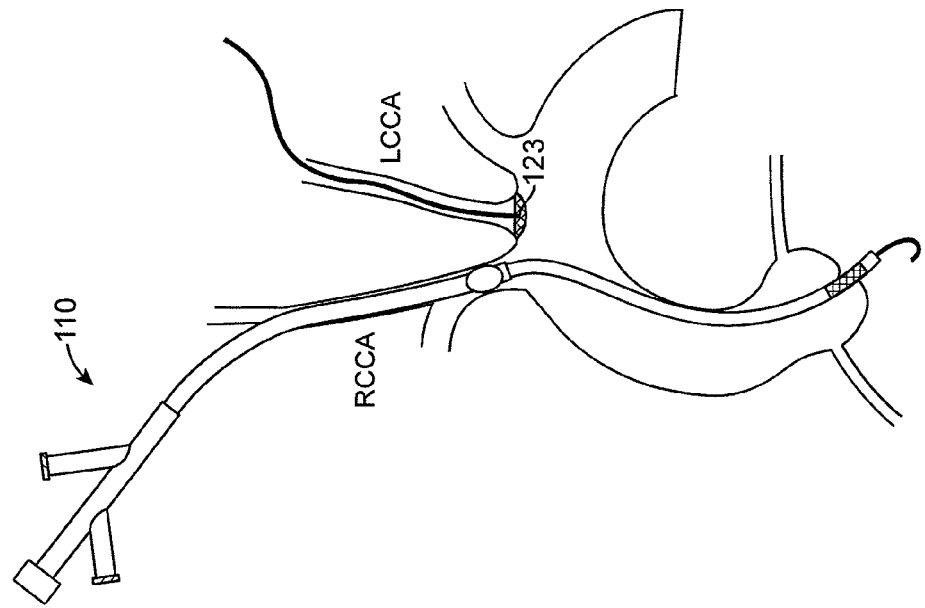
FIGS. 15A and 15B show embodiments wherein a filter is sized and shaped to be deployed across the ostium of the artery.
Figure 15A:
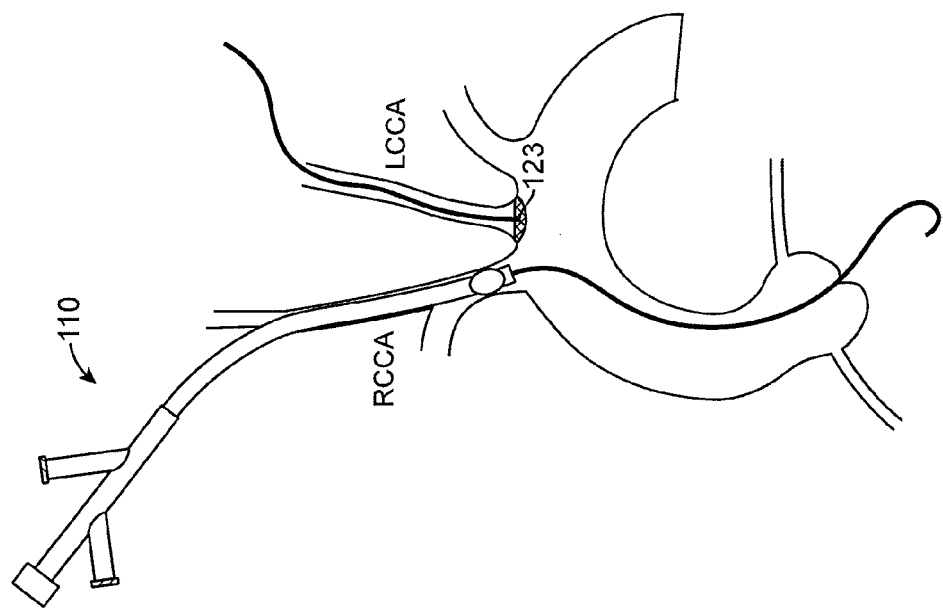

Various forms of embolic protection were described above including occlusion elements and filters. Additional embodiments that incorporate filters as means of embolic protection for all the head and neck vessels are now described. FIGS. 15A and 15B show embodiments wherein a filter 123 is sized and shaped to be deployed across the ostium of the artery (left carotid artery if the right carotid artery is accessed, or innominate artery if the left carotid artery is accessed.) The filter 123 can be placed via the contralateral carotid access site, or via a brachial or subclavian artery access site. Blood flow may proceed antegrade through the filter into the contralateral artery, while deflecting the flow of embolic particles away from the head and neck circulation.

Figure 16B:
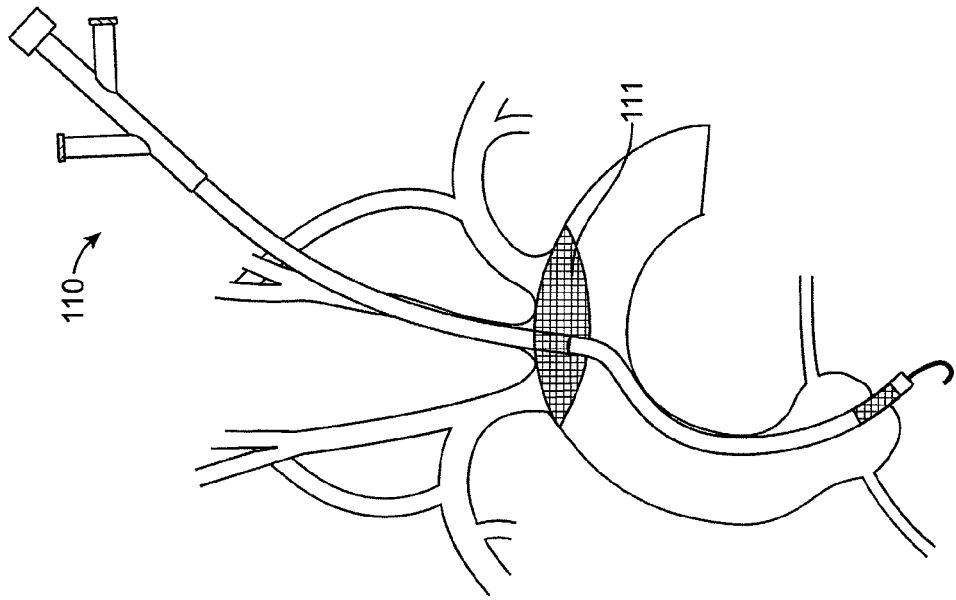
FIGS. 16A and 16B show embodiments wherein a filter is sized and shaped to be deployed in the aortic arch across the ostia of all the head and neck vessels.
Figure 16A:
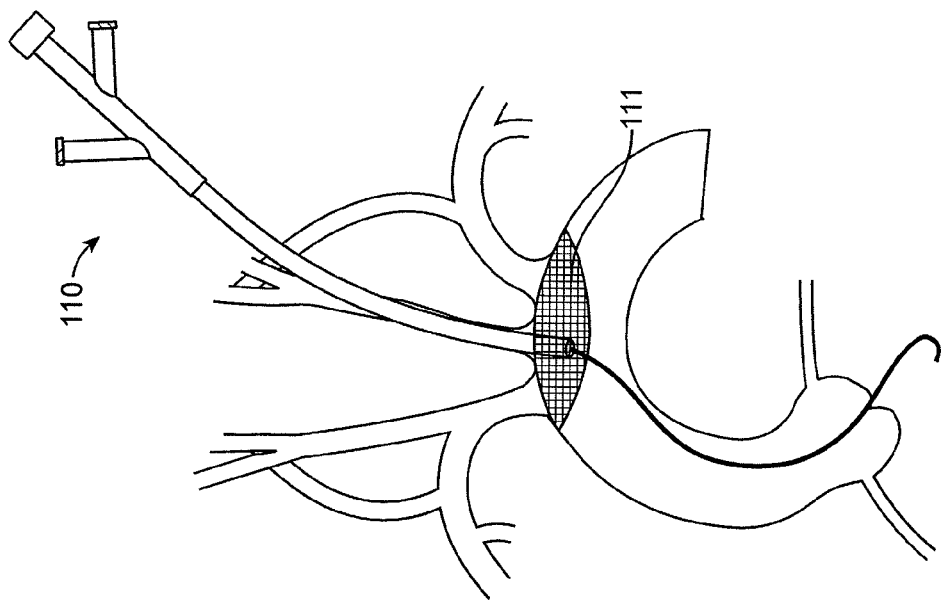
Figure 17B:
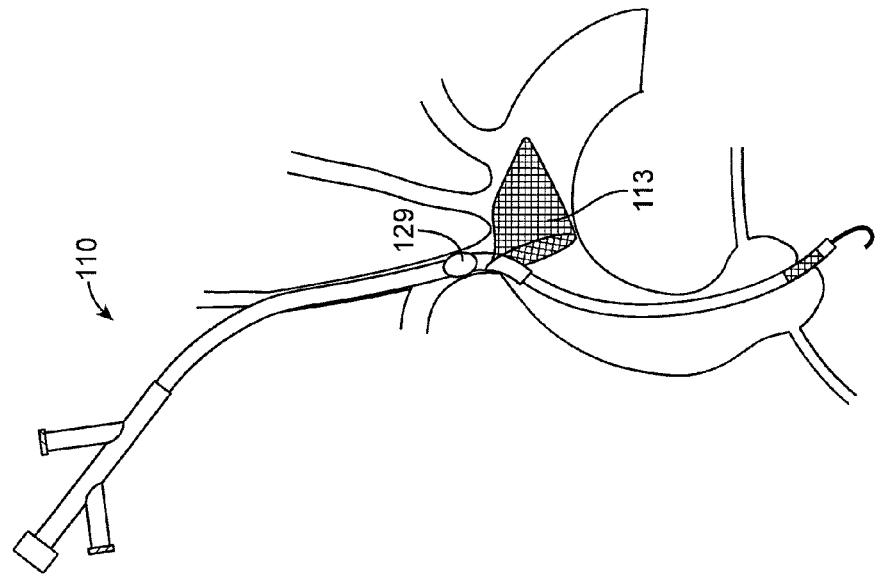
FIGS. 17A and 17B show embodiments wherein a filter is sized and shaped to be deployed within the aortic arch.
Figure 17A:
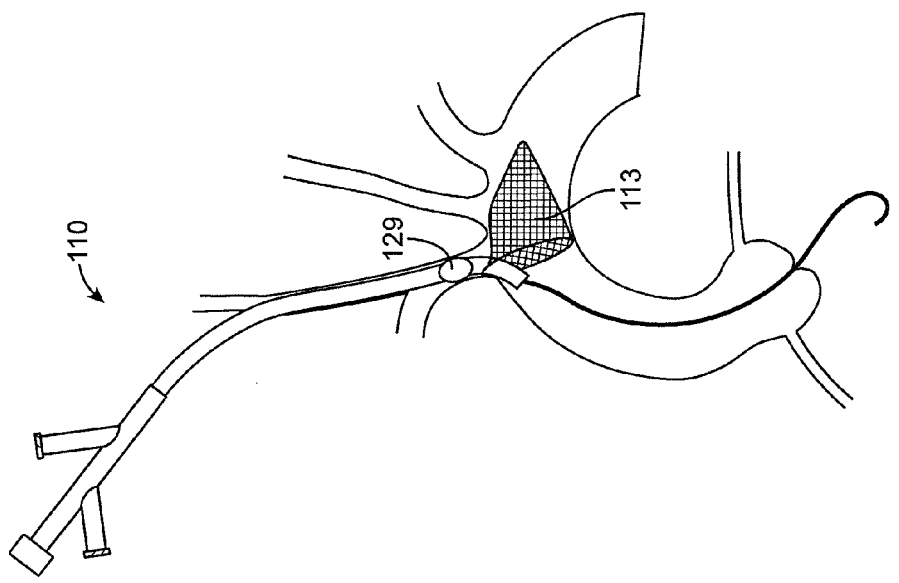

In another embodiment, shown in FIGS. 16A and 16B, a filter 111 is located on the access sheath 110, and is sized and shaped to be deployed in the aortic arch across all the head and neck vessels. In this embodiment, as both the access site carotid artery and the contralateral carotid artery are protected by the filter 111, an occlusion balloon is not required for embolic protection on the sheath during the valve implantation procedure. However, as there may be risk of embolic debris during deployment and retrieval of the filter, it may be desirable to retain the occlusion balloon and aspiration function as embolic protection during deployment of the filter prior to valve implantation, and retrieval of the filter after valve implantation. In another embodiment, shown in FIGS. 17A and 17B, an aortic embolic filter 113 is built into or on the access sheath 110 and is sized and shaped to be deployed within the aortic arch, so that all the head and neck vessels are protected by the filter 113 from embolic debris during the valve implantation procedure. An occlusion balloon 129 is attached to the sheath to block the artery. As described above, the occlusion balloon 129 and aspiration function are not needed during the procedure as the aortic filter protects the access vessel; however, as described above, occlusion and/or aspiration functions may be included in the system to provide protection during filter deployment and retrieval.

Figure 18A:
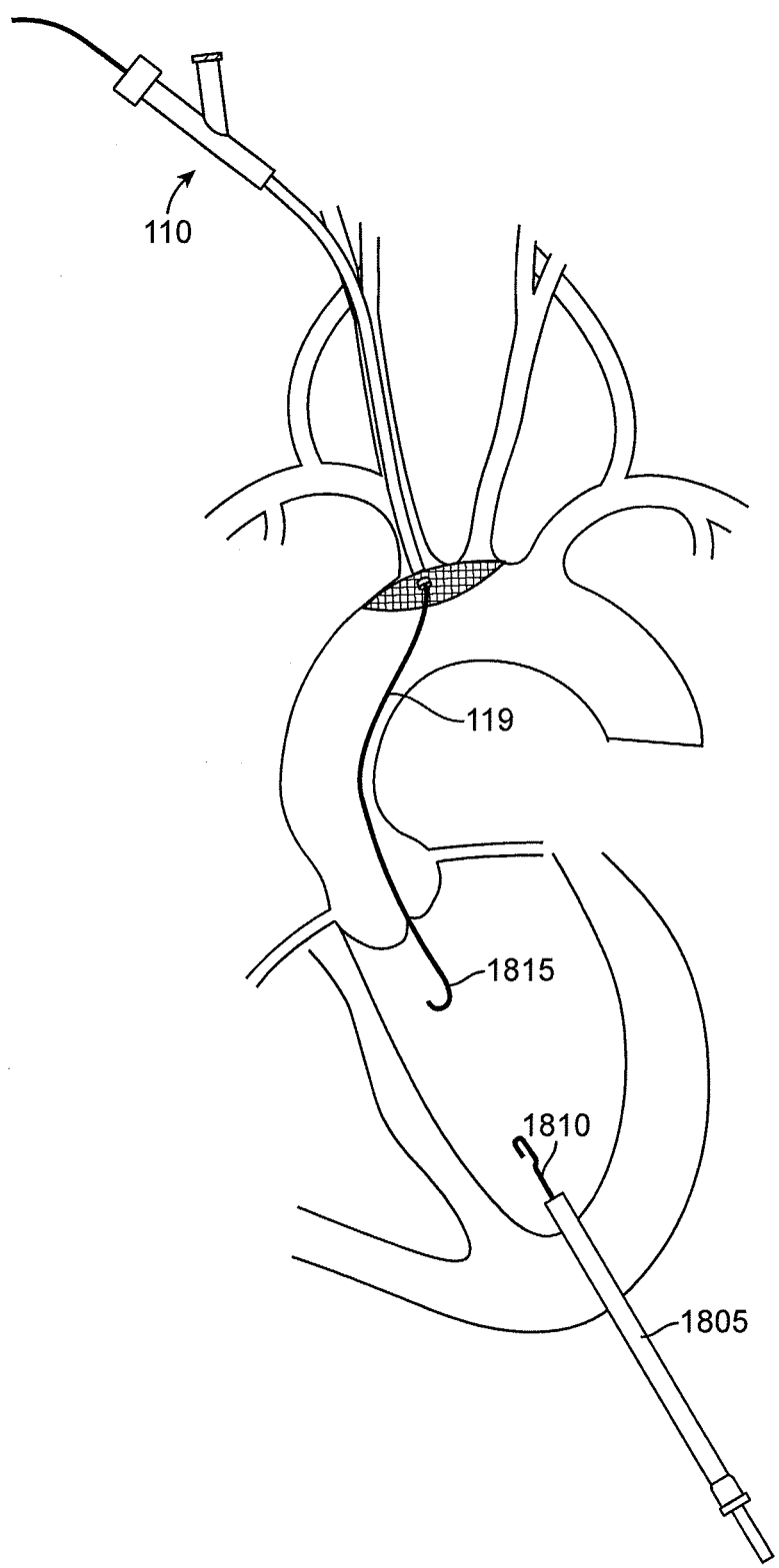
FIGS. 18A and 18B show alternate embodiments for delivering a prosthetic valve.
Figure 18B:
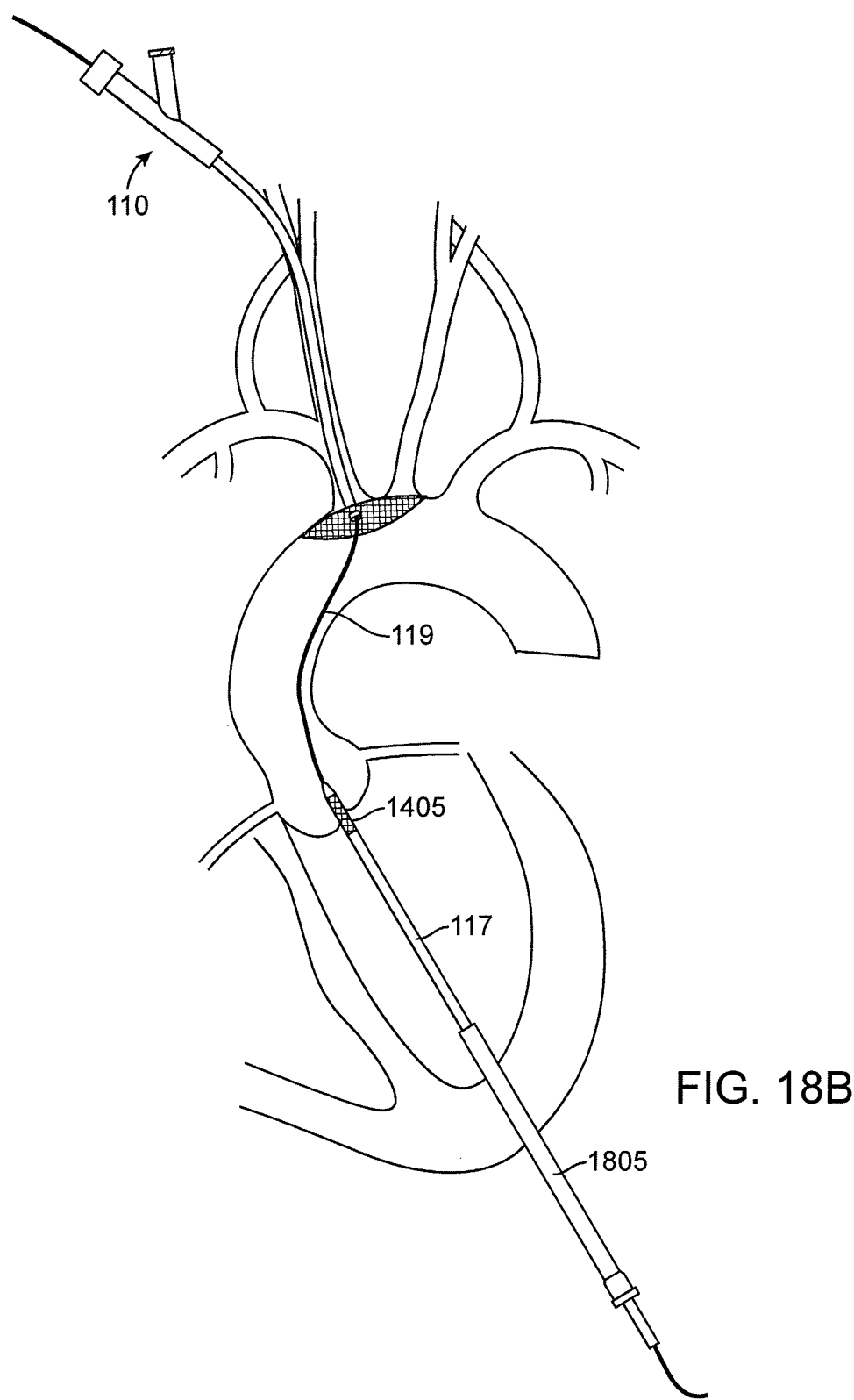

In yet another embodiment, shown in FIGS. 18A and 18B, a first access sheath 110 is deployed transcervically into the artery so as to provide access to the aortic valve. The first access sheath 110 is configured as described above so that it can be used to provide cerebral embolic protection and to introduce a guide wire 119 into the vasculature and across the aortic valve. In addition, a second access sheath 1805 is introduced via alternate access site to access the aortic annulus from the other side, for example a transapical access site into the left ventricle. The second access sheath 1805 can be used to introduce a delivery system 117 for implanting the prosthetic valve 1405. In this embodiment, the second access sheath 1805 may first be used to introduce a snare device 1810 that is configured to grasp or otherwise snare the distal end 1815 of the guide wire 119 that was inserted through the first access sheath 110, as in FIG. 18A. Alternately, the snare 1810 may be introduced via the first access sheath 110 and the guidewire 119 introduced via the second access sheath 1805. Irrespective of which end the guidewire was introduced or snared, the snare may be pulled back so that both ends of the guidewire may be secured externally. Such a double-ended securement of the guidewire 119 provides a more central, axially oriented and stable rail for placement of the prosthetic valve 1405 than in a procedure where the guidewire distal end is not secured. The prosthetic valve 1405 can then be positioned over the guidewire 119 via the second access sheath 1805, and deployed in the aortic annulus. In this embodiment, the first sheath 110 may be smaller than the second access sheath 1805, as the first sheath 110 does not require passage of a transcatheter valve.

Figure 19:
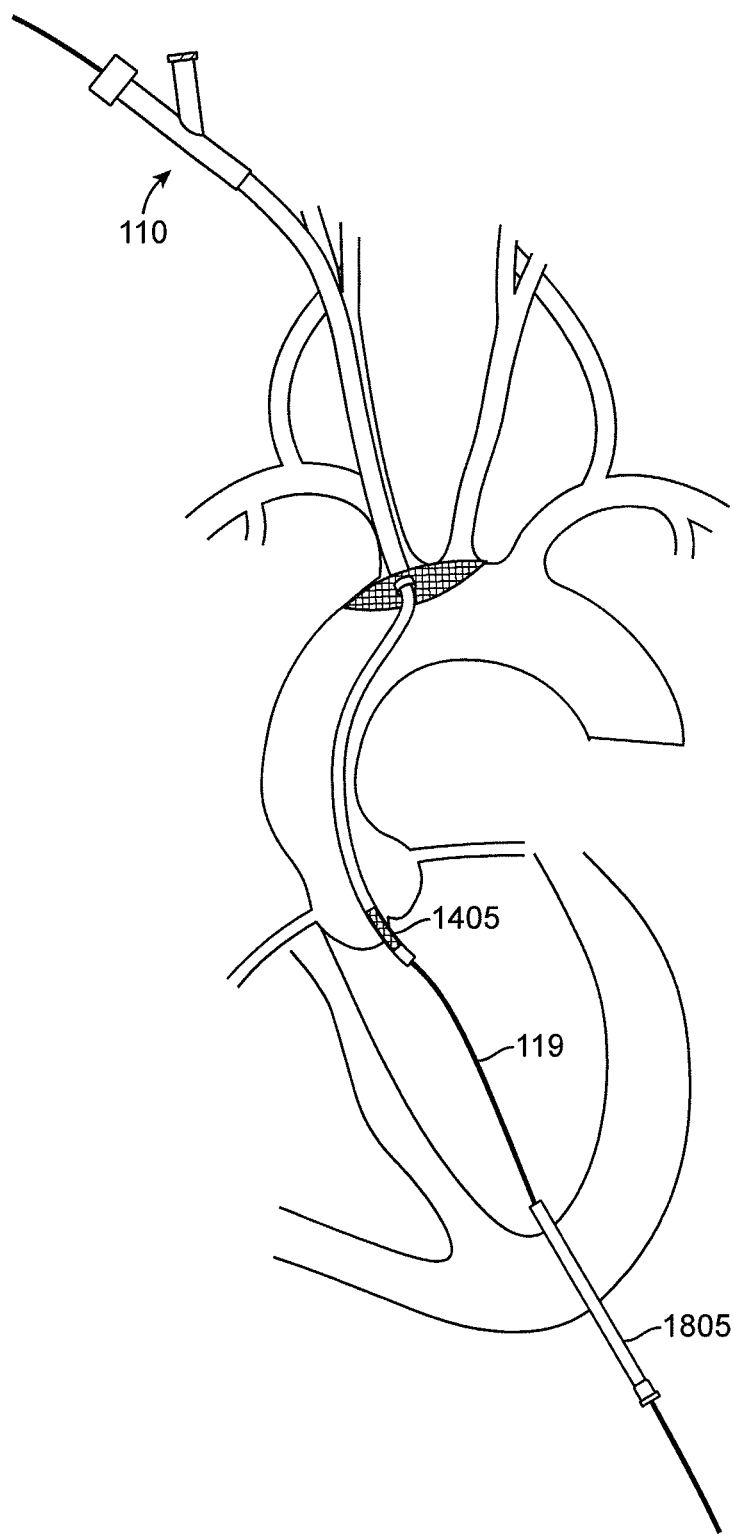
FIG. 19 shows another embodiment for delivering a prosthetic valve.

In a variation of the embodiment of FIGS. 18A and 18B, the prosthetic valve 1405 (and associated delivery system 117) may be delivered via the first sheath 110, as shown in FIG. 19. An advantage of this approach is that it requires a smaller puncture in the apex of the heart than the approach of FIGS. 18A and 18B. However a larger sheath is required in the first, access site.

Although the first access site is shown as a transcervical access in FIGS. 18 and 19, the first access site may also be a sub-clavian or transfemoral access site.

Any type of closing element, including a self-closing element, may be deployed about the penetration in the wall of the common carotid artery prior to withdrawing the sheath at the end of the procedure. Usually, the closing element will be deployed at or near the beginning of the procedure, but optionally, the closing element could be deployed as the sheath is being withdrawn, often being released from a distal end of the sheath onto the wall of the artery where the penetration occurs, such as the common carotid artery. Use of a self-closing element is advantageous since it affects substantially the rapid closure of the penetration in the common carotid artery as the sheath is being withdrawn. Such rapid closure can reduce or eliminate unintended blood loss either at the end of the procedure or during accidental dislodgement of the sheath. In addition, such a self-closing element may reduce the risk of arterial wall dissection during access. Further, the self-closing element may be configured to exert a frictional or other retention force on the sheath during the procedure. Such a retention force is advantageous and can reduce the chance of accidentally dislodging the sheath during the procedure. A self-closing element eliminates the need for vascular surgical closure of the artery with suture after sheath removal, reducing the need for a large surgical field and greatly reducing the surgical skill required for the procedure.

The disclosed systems and methods may employ a wide variety of closing elements, typically being mechanical elements which include an anchor portion and a closing portion such as a self-closing portion. The anchor portion may comprise hooks, pins, staples, clips, tine, suture, or the like, which are engaged in the exterior surface of the common carotid artery about the penetration to immobilize the self-closing element when the penetration is fully open. The self-closing element may also include a spring-like or other self-closing portion which, upon removal of the sheath, will close the anchor portion in order to draw the tissue in the arterial wall together to provide closure. Usually, the closure will be sufficient so that no further measures need be taken to close or seal the penetration. Optionally, however, it may be desirable to provide for supplemental sealing of the self-closing element after the sheath is withdrawn. For example, the self-closing element and/or the tissue tract in the region of the element can be treated with hemostatic materials, such as bioabsorbable polymers, collagen plugs, glues, sealants, clotting factors, or other clot-promoting agents. Alternatively, the tissue or self-closing element could be sealed using other sealing protocols, such as electrocautery, suturing, clipping, stapling, or the like. In another method, the self-closing element will be a self-sealing membrane or gasket material which is attached to the outer wall of the vessel with clips, glue, bands, or other means. The self-sealing membrane may have an inner opening such as a slit or cross cut, which would be normally closed against blood pressure. Any of these self-closing elements could be designed to be placed in an open surgical procedure, or deployed percutaneously.

In an embodiment, the closing element is a is a suture-based blood vessel closure device that can perform the dilation of an arteriotomy puncture, and therefore does not require previous dilation of the arteriotomy puncture by a separate device or by a procedural sheath dilator. The suture-based vessel closure device can place one or more sutures across a vessel access site such that, when the suture ends are tied off after sheath removal, the stitch or stitches provide hemostasis to the access site. The sutures can be applied either prior to insertion of a procedural sheath through the arteriotomy or after removal of the sheath from the arteriotomy. The device can maintain temporary hemostasis of the arteriotomy after placement of sutures but before and during placement of a procedural sheath and can also maintain temporary hemostasis after withdrawal of the procedural sheath but before tying off the suture. U.S. patent application Ser. No. 12/834,869 entitled "SYSTEMS AND METHODS FOR TREATING A CAROTID ARTERY", which is incorporated herein by reference in its entirety, describes exemplary closure devices and also describes various other devices, systems, and methods that are related to and that may be combined with the devices, systems, and methods disclosed herein.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A method of treating an aortic valve, comprising:
   forming a penetration at the neck of a patient in a wall of a common carotid artery;
   introducing an access sheath through the penetration;
   occluding the artery by inflation;
   inserting a guide wire through the access sheath and across the native aortic valve;
   introducing a prosthetic valve through the access sheath and percutaneously deploying the prosthetic valve at or near the position of the native aortic valve.

2. A method as in claim 1, wherein occluding the artery comprises inflating an occlusion balloon.

3. A method as in claim 1, further comprising:
   removing the access sheath;
   closing the penetration.

4. A method as in claim 1, further comprising applying a closure device at a site of the penetration before introducing the arterial access sheath through the penetration.

5. A method as in claim 4, wherein the closure device comprises a suture-based closure device.

6. A method as in claim 1, further comprising applying aspiration to the artery through the access sheath.

7. A method as in claim 6, further comprising regulating a rate of the aspiration.

8. A method as in claim 1, further comprising establishing passive blood flow from the artery such that blood flows into a lumen of the arterial access sheath and into a shunt connected to the access sheath.

9. A method as in claim 8, further comprising regulating the rate of passive flow from the artery.

10. A method as in claim 8, further comprising fluidly connecting the shunt to a collection reservoir or a venous return site in the patient.

11. A method as in claim 1, further comprising establishing retrograde blood flow through the artery such that blood flows into a lumen of the arterial access sheath and into a shunt connected to the access sheath.

* * * * *